(12) United States Patent
Pelssers et al.

(10) Patent No.: US 12,207,922 B2
(45) Date of Patent: Jan. 28, 2025

(54) METHOD AND APPARATUS FOR DIFFERENTIAL SWEAT MEASUREMENT

(71) Applicant: KONINKLIJKE PHILIPS N.V., Eindhoven (NL)

(72) Inventors: Eduard Gerard Marie Pelssers, Panningen (NL); Ron Martinus Laurentius Van Lieshout, Geldrop (NL); Mark Thomas Johnson, Arendonk (BE); Kiran Hamilton J. Dellimore, Utrecht (NL); Thomas Johannes Van Gijsel, Weert (NL)

(73) Assignee: Koninklijke Philips N.V., Eindhoven (NL)

( * ) Notice: Subject to any disclaimer, the term of this patent is extended or adjusted under 35 U.S.C. 154(b) by 822 days.

(21) Appl. No.: 17/275,499

(22) PCT Filed: Sep. 9, 2019

(86) PCT No.: PCT/EP2019/073951
§ 371 (c)(1),
(2) Date: Mar. 11, 2021

(87) PCT Pub. No.: WO2020/053129
PCT Pub. Date: Mar. 19, 2020

(65) Prior Publication Data
US 2022/0110557 A1    Apr. 14, 2022

(30) Foreign Application Priority Data
Sep. 11, 2018   (EP) ..................................... 18193693

(51) Int. Cl.
*A61B 5/145*    (2006.01)
*A61B 5/00*     (2006.01)

(52) U.S. Cl.
CPC ...... *A61B 5/14546* (2013.01); *A61B 5/14517* (2013.01); *A61B 5/4222* (2013.01); *A61B 5/4266* (2013.01); *A61B 5/6833* (2013.01)

(58) Field of Classification Search
CPC ............ A61B 10/0064; A61B 5/14521; A61B 5/4266; A61B 5/14517; A61B 5/14546; A61B 5/4222; A61B 5/6833
See application file for complete search history.

(56) References Cited

U.S. PATENT DOCUMENTS 8,215,192 B2    7/2012   Erez
2002/0115921 A1  8/2002   Berlin
(Continued)

FOREIGN PATENT DOCUMENTS

JP    2007000188 A    1/2007
WO    2015143259 A1   9/2015
(Continued)

OTHER PUBLICATIONS

International Search Report and Written Opinion, International Application No. PCT/EP2019/073951, Mailed on Dec. 2, 2019.
(Continued)

*Primary Examiner* — Eric J Messersmith

(57) ABSTRACT

Provided is a method of determining a concentration ($C_a$) of a first analyte (a) in sweat excreted by a first sweat gland type at a first skin location (i) having the first sweat gland type and a second sweat gland type. The method comprises measuring a first concentration (I) of the first analyte in sweat excreted at the first skin location and measuring at least one parameter of sweat excreted by the second sweat gland type at a second skin location (ii) having the second sweat gland type but not the first sweat gland type. The at least one parameter is used to determine a dilution factor (II) which quantifies dilution of the first analyte by sweat excreted by the second sweat gland type at the first skin
(Continued)

location. This dilution factor (II) is then used to correct the first concentration (I) so as to determine the concentration ($C_a$). Further provided is an apparatus (100) for determining the concentration ($C_a$).

9 Claims, 3 Drawing Sheets

(56) References Cited

U.S. PATENT DOCUMENTS

| | | | |
|---|---|---|---|
| 2003/0199743 A1* | 10/2003 | Berlin | G01N 33/57434 600/346 |
| 2015/0112165 A1 | 4/2015 | Heikenfeld | |
| 2016/0066894 A1* | 3/2016 | Barton-Sweeney | A61B 10/0012 600/301 |
| 2018/0020981 A1* | 1/2018 | Heikenfeld | A61B 5/6832 600/301 |

FOREIGN PATENT DOCUMENTS

| | | |
|---|---|---|
| WO | 2016007944 A2 | 1/2016 |
| WO | 2016197116 A1 | 12/2016 |
| WO | 2016207070 A1 | 12/2016 |
| WO | 2017070641 A1 | 4/2017 |
| WO | 2018057695 A1 | 3/2018 |

OTHER PUBLICATIONS

Taylor, N. et al., "Regional variations in transepidermal water loss, eccrine sweat gland density, sweat secretion rates and electrolyte composition in resting and exercising humans", Extrem. Physiol. Med., vol. 2, No. 1, Feb. 2013.

Mena-Bravo, A. et al., "Sweat: A sample with limited present applications and promisingfuture in metabolomics", Journal of Pharmaceutical and Biomedical Analysis, 2014.

Gao, W. et al., "Fully integrated wearable sensor arrays for multiplexed in situ perspiration analysis", Jan. 28, 2016 | vol. 529 | Nature | 509.

Z. Sonner, E. Wilder, J. Heikenfeld, G. Kasting, F. Beyette, D. Swaile, F. Sherman, J. Joyce, J. Hagen, N. Kelley-Loughnane, and R. Naik. The microfluidics of the eccrine sweat gland, including biomarker partitioning, transport, and biosensing implications. Biomicrofluidics 9, 031301 (2015).

K. Sato, W. H. Kang, K. Saga, and K. T. Sato, "Biology of sweat glands and their disorders. I. Normal sweat gland function," J. Am. Acad. Dermatol. 20, 537-563 (1989).

N. De Giovanni and N. Fucci, "The current status of sweat testing for drugs of abuse: A review," Curr. Med. Chem. 20, 545-561 (2013).

SCRAM Continuous Alcohol Monitoring, http://reliantmonitoring.com/work/scram-continuous-alcohol-monitoring#:~:text=SCRAM%20Continuous%20Alcohol%20Monitoring%20(SCRAM,single%2C%20court%2Dvalidated%20device., Accessed Mar. 10, 2021.

Wescor Nanoduct Neonatal sweat analysis system, Copyright 2006.

Bandodkar, A. J. et al. Epidermal tattoo potentiometric sodium sensors with wireless signal transduction for continuous non-invasive sweat monitoring. Biosens. Bioelectron. 54, 603-609 (2014).

Rose, D. P. et al. Adhesive RFID sensor patch for monitoring of sweat electrolytes. IEEE Trans. Biomed. Eng. 62, 1457-1465 (2015).

T. Guinovart, G. Valdes-Ramirez, J. R. Windmiller, F. J. Andrade, and J. Wang, "Bandage-based wearable potentiometric sensor for monitoring wound pH," Electroanalysis 26, 1345-1353 (2014.

Bandodkar, A. J. & Wang, J. "Non-invasive wearable electrochemical sensors: a review" Trends Biotechnol. 32, 363-371 (2014).

Kondo N, Takano S, Aoki K, Shibasaki M, Tominaga H, Inoue Y. Regional difference in the effect of exercise intensity on thermoregulatory sweating and cutaneous vasodilation. Acta Physiol Scand 1998, 164:71-78.

Éva Csösz1, Gabriella Emri2, Gergö Kalló1, George Tsaprailis3, and József Tözsér. Highly abundant defense proteins In human sweat as revealed by targeted proteomics and label free quantification mass spectrometry. J Eur Acad Dermatol Venereol. Oct. 2015 ; 29(10): 2024-2031. doi:10.1111/jdv.13221.

Chang-Yi Cui and David Schlessinger, Eccrine sweat gland development and sweat secretion Exp Dermatol. Sep. 2015 ; 24(9): 644-650. doi:10.1111/exd.12773.

Schittek B, Hipfel R, Sauer B, Bauer J, Kalbacher H, Stevanovic S, Schirle M, Schroeder K, Blin N, Meier F, Rassner G, Garbe C: Dermcidin: a novel human antibiotic peptide secreted by sweat glands. Nat Immunol 2001;2:1133-1137.

Shelley WB, Hurley HJ Jr., J Invest Dermatol. Apr. 1953;20(4):285-97. The physiology of the human axillary apocrine sweat gland.

Spearman, Richard Ian Campbell (1973). The Integument: A Textbook For Skin Biology. Biological Structure and Function Books. 3. CUP Archive. p. 137. ISBN 9780521200486.

A human axillary odorant is carried by apolipoprotein D. Zeng C, Spielman Al, Vowels BR, Leyden JJ, Biemann K, Preti G. Proc Natl Acad Sci U S A. Jun. 25, 1996;93(13):6626-30.

Labows, J.N., Preti, G., Hoelzle, E. et al. Steroid analysis of human apocrine secretion. Steroids 34, 249-258 (1979).

J Invest Dermatol. Jun. 1966;46(6):536-41. Histochemical demonstration of sialomucin in human eccrine sweat glands. Constantine VS1, Mowry RW.

Fitzpatrick's Dermatology in General Medicine, Eighth Edition, Copyright 2012.

Emelianow, Dermatopathology, Dec. 2011, Immunohistological pointers to a possible role for excessive cathelicidin (LL-37) expression by apocrine sweat glands in the pathogenesis of hidradenitis suppurativa/acne inversa.

* cited by examiner

METHOD AND APPARATUS FOR DIFFERENTIAL SWEAT MEASUREMENT

This application is the U.S. National Phase application under 35 U.S.C. § 371 of International Application No. PCT/EP2019/073951, filed on 9 Sep. 2019, which claims the benefit of European Application Serial No. 18193693.1, filed 11 Sep. 2018. These applications are hereby incorporated by reference herein.

FIELD OF THE INVENTION

This invention relates to a method and apparatus for determining the concentration of a sweat analyte.

BACKGROUND OF THE INVENTION

Non-invasive, semi-continuous and prolonged monitoring of biomarkers that indicate health and well-being is in demand. Such biomarker monitoring may, for example, find utility in the assessment of dehydration, stress, sleep, children's health and in perioperative monitoring. Sweat is a non-obtrusively accessible bio-fluid and is a rich source of information relating to the physiology and metabolism of the subject.

Some examples of clinically relevant components of sweat are $Na^+$, $Cl^-$ and/or $K^+$ ions to monitor dehydration, lactate as an early warning for inflammation (which is relevant to sepsis), glucose for diabetics and neonates, and cortisol in relation to sleep apnea and stress monitoring.

The development of reliable sweat sensing has, however, been hampered by several issues, in spite of clinical work showing promising results as early as the 1940s and 1950s. To date the impactful application of sweat analysis has been limited mainly to cystic fibrosis diagnostics, and drugs and alcohol abuse testing.

As summarized by Mena-Bravo and de Castro in "Sweat: A sample with limited present applications and promising future in metabolomics" J. Pharm. Biomed. Anal. 90, 139-147 (2014), it has been found that the results from sweat sensing can be highly variable, and a correlation between values determined from blood and sweat samples appears to be lacking for various biomarkers.

Efforts have been made to address these issues by bringing wearable sensors into nearly immediate contact with sweat as it emerges from the skin. An example is the wearable patch presented by Gao et al. in "Fully integrated wearable sensor arrays for multiplexed in situ perspiration analysis" Nature 529, 509-514 (2016). The patch includes a sensor array for measuring $Na^+$, $K^+$, glucose, lactate, and skin temperature. However, the focus of this study is on the development and integration of the sensors themselves which, whilst evidently crucial, does not address issues relating to sweat sample collection. The latter is mostly done by placing an absorbent pad with an area in the order of several $cm^2$ between the skin and the sensor. The assumption is that, providing ample sweat is produced (hence tests are done on individuals engaged in intense exercise), the pad will absorb the sweat for analysis, and newly generated sweat will refill the pad and 'rinse away' the old sweat. It is, however, likely that the time-dependent response of the sensor does not directly reflect the actual level of bio markers over time because of accumulation effects. The sample collection and presentation to the published sensors may not be well-controlled so that continuous reliable sensing over a long period of time is difficult. Such patches may also not be designed to handle the tiny amounts of sweat that are produced under normal conditions, i.e. in the order of nano liters per minute per sweat gland.

There are two types of sweat glands: apocrine and eccrine. An ongoing debate concerns a third type: the apoeccrine gland. The apocrine and eccrine glands respectively secrete specific biomarkers, referred to more generally herein as "analytes" in variable quantities. The diagnostic outcome arising from monitoring of such a sweat analyte may, for instance, depend on which gland was responsible for producing the detected analyte.

There are both anatomical and functional differences between apocrine and eccrine sweat glands. The secretory coil of the eccrine sweat glands consists of three different cell types which all play a role in production of sweat from eccrine sweat glands. One of these cell types, which can only be found in eccrine sweat glands, are the so-called "dark cells", which are cells that contain cytoplasmic electron-dense granules known for secreting various components such as glycoproteins, metals and the antimicrobial dermcidin. Dermcidin is an antimicrobial peptide secreted only by the eccrine sweat glands and directly attacks the bacteria on our skin. Dermcidin is one of the most abundant proteins in sweat, and is therefore a suitable marker for eccrine sweat glands. In addition, several proteins and peptides, e.g. cysteine proteinases, DNAse I, lysozyme, $Zn$-$\alpha 2$-glycoprotein, cysteine-rich secretory protein-3, have been identified in eccrine sweat. Dermcidin is not expressed in apocrine sweat glands.

Apocrine sweat glands can be found at a limited number of body locations, for instance the axilla. The apocrine gland secretes a translucent turbid viscous liquid onto the skin with a pH of 5 to 6.5, albeit in minute quantities. Unlike eccrine sweat glands, which secrete in a more regular manner, the apocrine glands secrete in periodic spurts. The apocrine sweat appears on the skin surface mixed with sebum, as sebaceous glands open into the same hair follicle. It is likely that the turbidity is caused by the non-dissolvable non-aqueous components, for instance the fatty acids of the sebum which are insoluble in water.

The apocrine glands have been found to be the only sweat gland type to excrete sweat containing certain analytes, including, without any limitation, apocrine secretion odour-binding proteins 1 and 2 (ASOB1 and ASOB2), certain carbohydrates, ferric ions, lipids, steroids, sialomucin (sialomucin was also found in sweat excreted by the eccrine glands, but in negligible amounts in comparison to apocrine sweat), and/or cathelicidin. It would be desirable to establish the concentration of sweat components as excreted by the apocrine glands in the apocrine sweat.

WO 2015/143259 A1 discloses a system and method for determining a user's physical condition.

US 2015/112165 A1 discloses devices that sense sweat and are capable of providing chronological assurance.

WO 2018/057695 A1 discloses a device for sensing a biofluid.

WO 2017/070641 A1 discloses devices and methods for buffering sweat samples.

SUMMARY OF THE INVENTION

The invention is defined by the claims.

According to an aspect there is provided a method of determining a corrected concentration ($C_a$) of a first analyte (a) in sweat excreted by a first sweat gland type at a first skin location (i) having the first sweat gland type and a second sweat gland type. In particular, this second sweat gland type may not excrete sweat containing the first analyte, or may excrete sweat having such a low concentration of first analyte (in comparison with the sweat excreted by the first sweat gland) that it can be neglected, or may excrete sweat at a concentration of first analyte which is prima facie significantly different from the concentration of the first analyte in the sweat excreted by the first sweat gland that the two concentrations can be easily distinguished, the method comprising: measuring a first concentration ($C_a^i$) of the first analyte in sweat excreted at the first skin location; measuring at least one parameter of sweat excreted by the second sweat gland type at a second skin location (ii) having the second sweat gland type but not the first sweat gland type; using the at least one parameter to determine a dilution factor ($D_a^i$) which quantifies dilution of the first analyte by sweat excreted by the second sweat gland type at the first skin location; and determining the corrected concentration ($C_a$) from the first concentration ($C_a^i$) using the dilution factor ($D_a^i$).

Various skin locations have both sweat glands of the first sweat gland type, e.g. the apocrine gland, and the second sweat gland type, e.g. the eccrine gland. When attempting to determine the concentration of a first analyte (a) in sweat excreted by glands of the first sweat gland type only at such a (first) skin location (i), the determination is hampered by the unknown, and potentially variable, dilution of the first analyte by the sweat excreted by glands of the second sweat gland type.

The present invention is based on the realisation that the dilution effect resulting from the sweat excreted by glands of the second sweat gland type at the first skin location (i) may be quantified by measuring at least one parameter of sweat excreted by the second sweat gland type at a second skin location (ii) which has the second sweat gland type but not the first sweat gland type. This is because the respective average secretion rates of glands of the second sweat gland type at the first and second skin locations may either be equal, for instance when the first and the second skin locations are relatively close together, or may at least be proportional to each other in a predictable way. Alternatively or additionally, the respective concentrations of a second analyte solely excreted by the second type of sweat gland at both the first skin location and second skin location may be equal, or proportional to each other. However at the first skin location, the measured concentration of the second analyte is lowered due to dilution by sweat of the first sweat gland type. By measuring the concentration of the second analyte at both skin locations, the dilution at the first skin location may be determined and this also enables determination of the dilution of the first analyte at the first skin location.

This enables determination of a dilution factor ($D_a^i$) quantifying dilution of the first analyte by sweat excreted by the second sweat gland type at the first skin location (i) using the at least one parameter of sweat excreted by the second sweat gland type at the second skin location (ii). This dilution factor factor ($D_a^i$) is then used to correct a measured first concentration ($C_a^i$) of the first analyte for dilution by the sweat excreted by glands of the second sweat gland type at the first skin location (i).

The at least one parameter may include a flow rate of sweat from the second sweat gland type at the second skin location. Measuring the flow rate of sweat from the second sweat gland type at the second skin location may provide a relatively simple means of determining the dilution factor ($D_a^i$). Using the flow rate to determine the dilution factor ($D_a^i$) may comprise using a predetermined correlation between the flow rate and the dilution factor ($D_a^i$). In practice, the predetermined correlation may be used in the form of a graph or look-up table.

The method may further comprise measuring a second concentration ($C_e^i$) of a second analyte (e) in sweat excreted at the first skin location (i). The second analyte may be in sweat excreted by the second sweat gland type, and may not be in sweat excreted by the first sweat gland type, or may be excreted with such a low concentration of second analyte in sweat (in comparison with the one from the sweat excreted by the second sweat gland) that it can be neglected or may be excreted at a concentration of second analyte in sweat which is such prima facie significantly different from the concentration of the second analyte in the sweat excreted by the second sweat gland that the two concentrations can be easily distinguished. In this embodiment, the at least one parameter includes a third concentration ($C_e^{ii}$) of the second analyte in sweat excreted at the second skin location (ii), and using the at least one parameter to determine the dilution factor ($D_a^i$) comprises calculating the dilution factor using the second concentration ($C_e^i$) and the third concentration ($C_e^{ii}$). The dilution factor ($D_a^i$) may, for example, be calculated using the following equation:

$$D_a^i = 1 - \frac{C_e^i}{C_e^{ii}}. \quad \text{(Equation I)}$$

The determining the corrected concentration ($C_a$) from the first concentration ($C_a^i$) using the dilution factor ($D_a^i$) may comprise using the following equation:

$$C_a = \frac{C_a^i}{D_a^i}. \quad \text{(Equation II)}$$

The method may further comprise: calculating a ratio ($R_{act}$) between a first local activation level of glands of the second sweat gland type at the first skin location and a second local activation level of glands of the second sweat gland type at the second skin location; and generating a value using the at least one parameter and the ratio ($R_{act}$), wherein the using the at least one parameter to determine the dilution factor ($D_a^i$) comprises using the value. The ratio ($R_{act}$) may be used to correct for any differences between the respective local sweat gland activation levels at the first (i) and second (ii) skin locations, e.g. where the first and second skin locations are relatively far apart from each other. The ratio ($R_{act}$) may, for instance, be calculated using the following equation:

$$R_{act} = \frac{SR_i^e \cdot GD_{ii}^e}{SR_{ii}^e \cdot GD_i^e}; \quad \text{(Equation III)}$$

wherein $SR_i^e$ and $SR_{ii}^e$ are local sweat rates for the glands of the second sweat gland type at the first (i) and second (ii) skin locations respectively, and $GD_i^e$ and $GD_{ii}^e$ are local densities of the glands of the second sweat gland type at the first (i) and second (ii) skin locations respectively.

According to another aspect there is provided an apparatus for determining a corrected concentration ($C_a$) of a first analyte (a) in sweat excreted by a first sweat gland type at a first skin location (i) having the first sweat gland type and a second sweat gland type which may not excrete sweat containing the first analyte, or may excrete sweat having such a low concentration of first analyte (in comparison with the sweat excreted by the first sweat gland) that it can be neglected, or may excrete sweat at a concentration of first analyte which is prima facie significantly different from the concentration of the first analyte in the sweat excreted by the first sweat gland that the two concentrations can be easily distinguished, the apparatus comprising: a first sensor for measuring a first concentration ($C_a^i$) of the first analyte in sweat excreted at the first skin location; and a second sensor for measuring at least one parameter of sweat excreted by the second sweat gland type at a second skin location (ii) having the second sweat gland type but not the first sweat gland type.

The apparatus may comprise a first sweat collection hole for supplying the first sensor with sweat, and a second sweat collection hole for supplying the second sensor with sweat. The first and second sweat collection holes may thus be independent of each other, thereby to enable independent sweat sampling from the respective first and second skin locations.

The distance between the respective sweat collection holes may be at least partly determined by intended sampling location(s). The distance separating the first and second sweat collection holes from each other may be, for example, at least about 1 cm, such as at least about 2 cm.

When, for example, the first and second sweat sensors are included in a single patch, the first and second sweat collection holes may be separated from each other by at least about 1 cm, preferably by at least about 2 cm.

Irrespective of whether the first and second sweat sensors are included in a single patch, the first and second collection holes may each, for example, have a maximum area of about 2 cm², such as an area of about 1 cm².

The second sensor may comprise a flow rate sensor and the at least one parameter may thus include a flow rate of sweat from the second sweat gland type at the second skin location. The flow rate sensor may provide a relatively simple means of determining the dilution factor ($D_a^i$). The apparatus may only require the first sensor and the flow rate sensor to enable determination of the corrected concentration ($C_a$). Such an apparatus may therefore be relatively simple and inexpensive to manufacture.

The apparatus may comprise a third sensor for measuring a second concentration ($C_e^i$) of a second analyte (e) in sweat excreted at the first skin location (i). The second analyte may be in sweat excreted by the second sweat gland type and may not be in sweat excreted by the first sweat gland type or may be excreted with such a low concentration of second analyte in sweat (in comparison with the one from the sweat excreted by the second sweat gland) that it can be neglected or may be excreted at a concentration of second analyte in sweat which is such prima facie significantly different from the concentration of the second analyte in the sweat excreted by the second sweat gland that the two concentrations can be easily distinguished. In this embodiment, the second sensor comprises a detector for measuring a third concentration ($C_e^{ii}$) of the second analyte in sweat excreted at the second skin location (ii), and the at least one parameter includes the third concentration.

The first sensor and the second sensor may be included in a single patch for attaching to the first and second skin locations when the first skin location (i) is adjacent the second location (ii). Alternatively, the first sensor may be included in a first patch for attaching to the first skin location (i) and the second sensor may be included in a second patch for attaching to the second skin location (ii).

The single patch or the pair of first and second patches may, for instance, be positioned either side of the border between the armpit area comprising apocrine glands (with hairs) and the adjacent area without apocrine glands (without hairs). This border is relatively sharp and therefore a distance separating the sweat collection holes of 2 cm as minimum may suffice. It may be desirable to sample from a relatively flat skin area to aid positioning of the (single) patch in a suitable fashion, taking account of the muscles below the skin and that smaller people have also relatively small armpit areas. In this regard, a hole size which has a maximum area of around 1-2 cm² is practical at the armpit side. On the adjacent area such restrictions are less strict, since the area may be smoother and flatter, but also here a hole having a maximum area of 1-2 cm² may suffice.

The apparatus may further include a controller configured to: use the at least one parameter to determine a dilution factor ($D_a^i$) corresponding to dilution of the first analyte by sweat excreted by the second sweat gland type at the first skin location; and determine the corrected concentration ($C_a$) from the first concentration ($C_a^i$) using the dilution factor ($D_a^i$).

The apparatus may, for instance, include a user interface for displaying the corrected concentration ($C_a$) determined by the controller.

When the second sensor comprises the flow rate sensor, the controller may be configured to determine the dilution factor ($D_a^i$) using a predetermined correlation between the flow rate and the dilution factor ($D_a^i$). In practice, the controller may use the predetermined correlation in the form of a graph or look-up table.

When the apparatus includes the third sensor and the detector, the controller may be configured to calculate the dilution factor using the second concentration ($C_e^i$) and the third concentration ($C_e^{ii}$). The dilution factor ($D_a^i$) may, for example, be calculated by the controller using the following equation:

$$D_a^i = 1 - \frac{C_e^i}{C_e^{ii}}; \quad \text{(Equation I)}$$

The corrected concentration ($C_a$) may be calculated by the controller from the dilution factor ($D_a^i$) and the first concentration ($C_a^i$) using the following equation:

$$C_a = \frac{C_a^i}{D_a^i}. \quad \text{(Equation II)}$$

The controller may be configured to: calculate a ratio ($R_{act}$) between a first local activation level of glands of the second sweat gland type at the first skin location and a second local activation level of glands of the second sweat gland type at the second skin location; and generate a value using the at least one parameter and the ratio ($R_{act}$). In this embodiment, the controller is configured to determine the dilution factor ($D_a^i$) using the value. The ratio ($R_{act}$) may be used to correct for any differences between the respective local sweat gland activation levels at the first and second skin locations, e.g. where the first and second skin locations are relatively far apart from each other. The ratio ($R_{act}$) may, for instance, be calculated by the controller using the following equation:

$$R_{act} = \frac{SR_i^e \cdot GD_{ii}^e}{SR_{ii}^e \cdot GD_i^e};$$ (Equation III)

wherein $SR_i^e$ and $SR_{ii}^e$ are local sweat rates for the glands of the second sweat gland type at the first (i) and second (ii) skin locations respectively, and $GD_i^e$ and $GD_{ii}^e$ are local densities of the glands of the second sweat gland type at the first (i) and second (ii) skin locations respectively.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
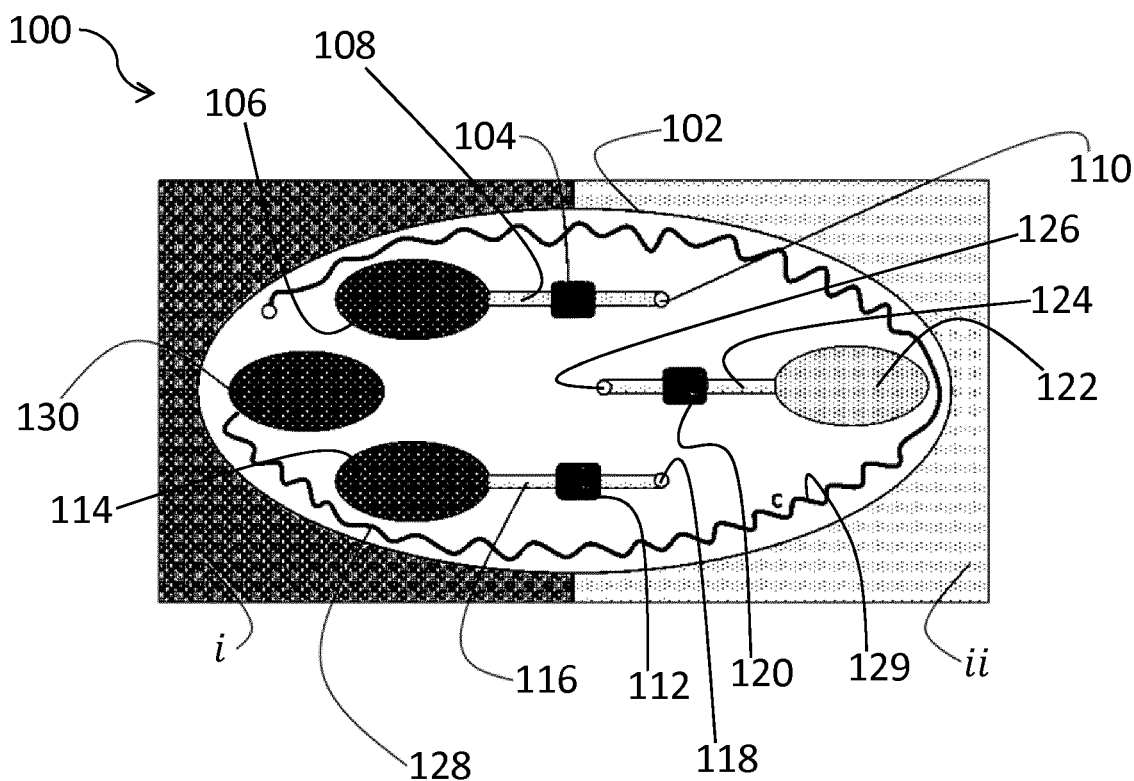
FIG. 1 shows an apparatus according to an embodiment.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a method of determining a concentration ($C_a$) of a first analyte (a) in sweat excreted by a first sweat gland type at a first skin location (i) having the first sweat gland type and a second sweat gland type which does not excrete sweat containing the first analyte. The method comprises measuring a first concentration ($C_a^i$) of the first analyte at the first skin location and measuring at least one parameter of sweat excreted by the second sweat gland type at a second skin location (ii) having the second sweat gland type but not the first sweat gland type. The at least one parameter is used to determine a dilution factor ($D_a^i$) which quantifies dilution of the first analyte by sweat excreted by the second sweat gland type at the first skin location. This dilution factor ($D_a^i$) is then used to correct the first concentration ($C_a^i$) so as to determine the concentration ($C_a$).

Various skin locations have both sweat glands of the first sweat gland type, e.g. the apocrine gland, and the second sweat gland type, e.g. the eccrine gland. When attempting to determine the concentration of a first analyte (a) excreted by glands of the first sweat gland type only at such a (first) skin location (i), the determination is hampered by the unknown, and potentially variable, dilution of the first analyte by the sweat excreted by glands of the second sweat gland type.

The present invention is based on the realisation that the dilution effect resulting from the sweat excreted by glands of the second sweat gland type at the first skin location (i) may be quantified by measuring at least one parameter of sweat excreted by the second sweat gland type at a second skin location (ii) which has the second sweat gland type but not the first sweat gland type. This is because the respective average secretion rates of glands of the second sweat gland type at the first and second skin locations may either be equal, for instance when the first and the second skin locations are relatively clo se together, or may at least be proportional to each other in a predictable way. Alternatively or additionally, the respective concentrations of a second analyte solely excreted by the second type of sweat gland at both the first skin location and second skin location may be equal, or proportional to each other. However at the first skin location, the measured concentration of the second analyte is lowered due to dilution by sweat of the first sweat gland type. By measuring the concentration of the second analyte at both skin locations, the dilution at the first skin location may be determined and this also enables determination of the dilution of the first analyte at the first skin location.

This enables determination of a dilution factor ($D_a^i$) quantifying dilution of the first analyte by sweat excreted by the second sweat gland type at the first skin location (i) using the at least one parameter of sweat excreted by the second sweat gland type at the second skin location (ii). This dilution factor factor ($D_a^i$) is then used to correct a measured first concentration ($C_a^i$) of the first analyte for dilution by the sweat excreted by glands of the second sweat gland type at the first skin location (i).

The present invention thus provides a differential measuring method (and a related apparatus) for determining the corrected concentration ($C_a$). The first skin location (i) may, for instance, have apocrine and eccrine glands. By measuring the first concentration ($C_a^i$) at the first skin location (i) of the first analyte (a) solely originating from apocrine glands (although at this stage diluted to an unknown degree by the eccrine glands at the the first skin location (i)) and measuring the parameter of sweat excreted by the eccrine glands at the second skin location (ii) which has eccrine glands only, the undiluted concentration of the first analyte (a) in the apocrine sweat may be determined unambiguously.

There is still a debate ongoing about the existence of a third gland type in the axilla: the apoeccrine gland. For present purposes, the first sweat gland type may, for instance, be regarded as including both the apocrine and apoeccrine glands. In this case, the second sweat gland type would correspond to the eccrine gland.

FIG. 1 shows an apparatus 100 according to an embodiment. The apparatus 100 comprises a single patch 102 which is positioned on, e.g. adhered to, a first skin location i, as represented by the darker pattern on the left hand side of FIG. 1, and a second skin location ii which is adjacent the first skin location i. A single patch 102 spanning the adjacent first i and second ii skin locations may mean that the respective average secretion rates of glands of the second sweat gland type at the first i and second ii skin locations may be equal, or close to equal, which may simplify calculation of the dilution factor ($D_a^i$). Alternatively, the apparatus 100 may include two separate patches, e.g. for respectively attaching to non-adjacent first i and second ii skin locations.

Figure 2:
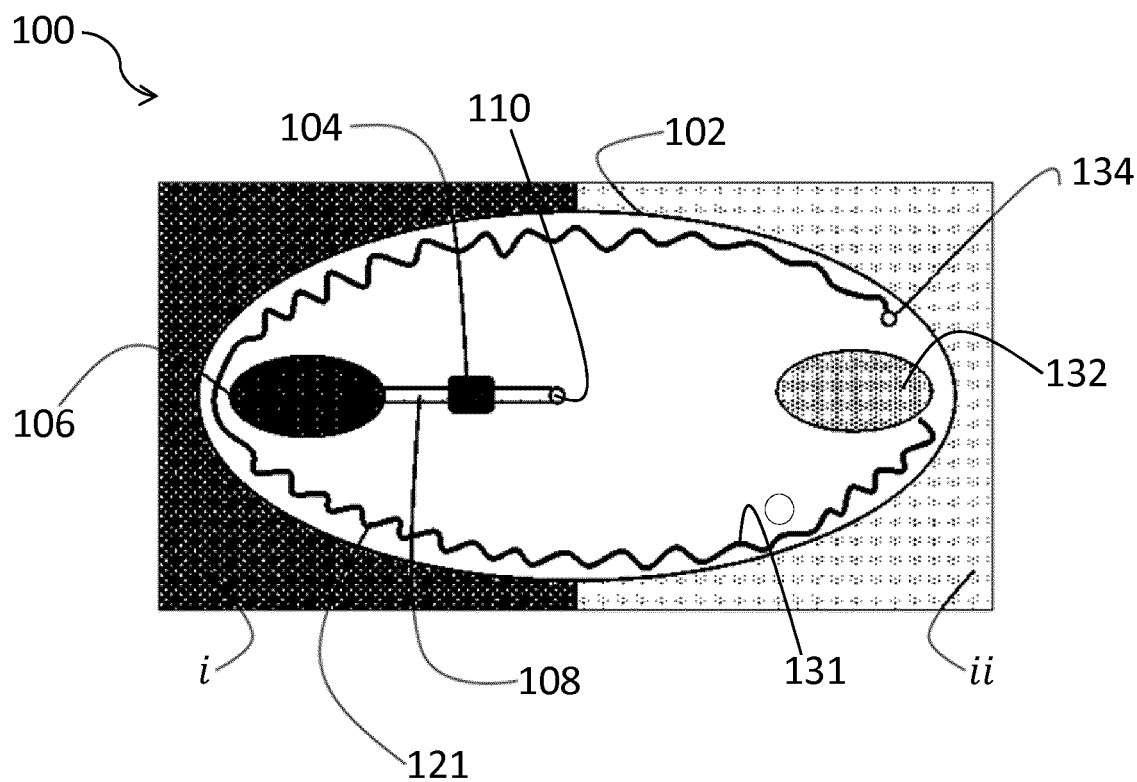
FIG. 2 shows an apparatus according to another embodiment.

Whilst not apparent from the plan view provided in FIGS. 1 and 2, the patch 102 may include a first layer which contacts the skin and a second layer disposed on the first layer, such that the first layer is effectively interposed between the skin and the second layer. The second layer may cover the various sweat sampling and sensing components of the patch 102.

As shown in FIG. 1, the apparatus 100 comprises a first sensor 104. The first sensor 104 is for measuring a first concentration ($C_a^i$) of the first analyte at the first skin location i. Sweat is collected from the first skin location i by a first collection hole 106 in the first layer and transported to the first sensor 104 via a channel 108. The channel 108 extends past the first sensor 104 and terminates at an air vent 110 delimited by the second layer.

The first sensor 104 may employ any suitable analyte concentration measurement principle, providing the first sensor 104 is able to measure the concentration of the first analyte (a). For example, colorimetry, electrical impedance, labelled antibodies, etc. may be used in the concentration measurement of the first analyte (a). A technique using labelled antibodies may, for instance, be used for protein concentration determination for specific proteins.

A second sensor 120, 121 is provided in the apparatus 100 for measuring the at least one parameter of sweat excreted by the second sweat gland type at the second skin location ii, which has the second sweat gland type but not the first sweat gland type.

In the embodiment shown in FIG. 1, the second sensor includes a detector 120 for measuring a (third) concentration ($C_e^{ii}$) of the second analyte at the second skin location ii. The detector 120 is supplied with sweat by the channel 124 extending between the second collection hole 122, which receives sweat from the second skin location ii, and the detector 120. The channel 124 further extends beyond the detector 120, and terminates at the air vent 126.

The distance between the first and second sweat collection holes 106, 122 (132 in FIG. 2) may be at least partly determined by intended sampling location(s). The distance separating the first and second sweat collection holes 106, 122 (132 in FIG. 2) from each other may be, for example, at least about 1 cm, such as at least about 2 cm.

When, for example, the first sweat sensor 104 and the second sweat sensor 120, 121 are included in a single patch, the first and second sweat collection holes 106, 122 (132 in FIG. 2) may be separated from each other, i.e. the distance between the respective edges of the sweat collection holes 106, 122 (132 in FIG. 2), by at least about 1 cm, such as at least about 2 cm.

Irrespective of whether the first and second sweat sensors 104, 120, 121 are included in a single patch, the first and second collection holes 106, 122 (132 in FIG. 2) may each, for example, have a maximum area of about 2 cm², such as an area of about 1 cm².

The detector 120 may employ any suitable analyte concentration measurement principle, providing the detector 120 is able to measure the (third) concentration ($C_e^{ii}$) of the second analyte (e) at the second skin location ii. For example, colorimetry, electrical impedance, labelled antibodies, etc. may be used in the concentration measurement of the second analyte (e).

In the embodiment shown in FIG. 1, a third sensor 112 is provided for measuring a (second) concentration ($C_e^i$) of a second analyte (e) at the first skin location i. The second analyte may be in sweat excreted by the second sweat gland type and may not be in sweat excreted by the first sweat gland type. The third sensor 112 is supplied with sweat by the channel 116 extending between the further first collection hole 114, which receives sweat from the first skin location i, and the third sensor 112. The channel 116 further extends beyond the third sensor 112, and terminates at the air vent 118.

The third sensor 112 may employ any suitable analyte concentration measurement principle, providing the third sensor 112 is able to measure the (second) concentration ($C_e^i$) of the second analyte (e) at the first skin location i. For example, colorimetry, electrical impedance, labelled antibodies, etc. may be used in the concentration measurement of the second analyte (e).

An optional flow rate analyser 128 may be included in the apparatus 100, as shown in FIG. 1. This flow rate analyser 128 may, for instance, comprise a thin channel 129 extending around the patch 102. The thin channel 129, which is progressively filled with sweat via an additional collection hole 130 at the first skin location i, provides an indication of the flow rate from the first skin location i by measurement of the length of the thin channel 129 which becomes filled with sweat as a function of time. The term "thin" in this context (and in relation to the flow rate sensor 121) refers to the channel 129 being thinner, i.e. having a relatively smaller diameter bore, in comparison to the channels 108, 116 and 124 which are intended to carry sweat to the respective sensor/detector 104, 116 and 120, rather than providing an indication of flow rate.

Any suitable detection principle may be used to measure the degree of filling of the thin channel 129. For example, the position of the meniscus in the thin channel 129 as a function of time may be determined from a suitable image. In this respect, the flow rate analyser 128 may include a camera (not shown), and the apparatus 100 may, for instance, include a controller (not shown in FIGS. 1 and 2) loaded with suitable image analysing software for detecting the meniscus. Alternative flow rate sensing principles may also be contemplated, such as calorimetric flow sensing, temperature gradient driven flow sensing, etc.

Whilst the flow rate analyser 128 may be useful due to the dependency of concentrations of particular components on the sweat rate, this flow rate analyser 128 is not essential in the context of the embodiment shown in FIG. 1 for determining the dilution factor ($D_a^i$) which quantifies dilution of the first analyte by sweat excreted by the second sweat gland type at the first skin location i. The dilution factor ($D_a^i$) may be derived using the second concentration ($C_e^{ii}$) and the third concentration ($C_e^{ii}$), as respectively measured by the third sensor 112 and the detector 120 in the apparatus 100 as depicted in FIG. 1, as will now be explained in more detail.

The first concentration ($C_a^i$) of the first analyte (a) at the first skin location i, as measured using the first sensor 104, may be expressed in terms of the dilution factor ($D_a^i$) and the corrected concentration ($C_a$) in the following way:

$$C_a^i = C_a \cdot D_a^i \qquad \text{(Equation A)}.$$

Similarly, the second concentration ($C_e^i$) of the second analyte (e) at the first skin location i, as measured using the third sensor 112, may be expressed in terms of a further dilution factor ($D_e^i$), which quantifies dilution of the second analyte (e) by sweat excreted by the first sweat gland type at the first skin location i, and a corrected concentration of the second analyte ($C_e$) in the following way:

$$C_e^i = C_e \cdot D_e^i \qquad \text{(Equation B)}.$$

The respective dilution factors $D_a^i$ and $D_e^i$ both have values between 0 and 1, and are related to each other by the following equation:

$$D_a^i + D_e^i = 1 \qquad \text{(Equation C)}.$$

Equation C reflects the mutual dilution of the respective sweats excreted by the first and second sweat gland types at the first skin location i. Combining Equations B and C gives:

$$D_a^i = 1 - \frac{C_e^i}{C_e^{ii}}. \quad \text{(Equation D)}$$

It may be assumed that the undiluted concentration of the second analyte (e) in sweat of the second sweat gland type only at the first skin location i (i.e. correcting for the diluting effect of the sweat from the first sweat gland type) is equal, or at least very similar, to the concentration of the second analyte (e) at the second skin location ii, i.e.

$$C_e = C_e^{ii} \quad \text{(Equation E);}$$

This assumption holds particularly when the first and second locations i and ii are relatively close to each other, as may be the single patch 102 embodiments depicted in FIGS. 1 and 2, providing that the patch 102 has an area, for example, in the order of only a few cm². Note that in Equation E, $C_e^{ii}$ is the (third) concentration of the second analyte (e) at the second skin location ii. Substituting Equation E in Equation D gives Equation I:

$$D_a^i = 1 - \frac{C_e^i}{C_e^{ii}}. \quad \text{(Equation I)}$$

Using Equation I, the second concentration ($C_e^i$) and the third concentration ($C_e^{ii}$) measured using the third sensor 112 and the detector 120 respectively, the dilution factor ($D_a^i$) may thus be determined. The corrected concentration ($C_a$) may then be calculated from the dilution factor ($D_a^i$) and the first concentration ($C_a^i$) using Equation II (obtained by rearranging Equation A):

$$C_a = \frac{C_a^i}{D_a^i}. \quad \text{(Equation II)}$$

The units of the corrected concentration ($C_a$), the first concentration ($C_a^i$), the second concentration ($C_e^i$) and the third concentration ($C_e^{ii}$) may all be, for instance, mol/L. Whilst not essential, measuring a total sweat flow rate using the flow rate analyser 128 may permit assessment of the mean quantity of sweat that the subject is excreting, which may be used to refine the above calculations.

Whilst not shown in FIG. 1, the apparatus 100 may optionally include a flow rate sensor for measuring a flow rate of sweat from the second sweat gland type at the second skin location ii. Such a flow rate sensor may be an alternative or in addition to the flow rate analyser 128. Such a flow rate sensor may, as will be described in more detail in relation to FIG. 2, provide an alternative means for estimating the dilution factor ($D_a^i$). This may, for example, provide verification or enable refinement of the dilution factor ($D_a^i$) derived from measuring the second $C_e^i$ and third $C_e^{ii}$ concentrations of the second analyte (e).

Turning to FIG. 2, an apparatus 100 according to an alternative embodiment is depicted. As in the case of FIG. 1, the apparatus 100 comprises a single patch 102 which is positioned on, e.g. adhered to, the first skin location i, as represented by the darker pattern on the left side of the apparatus 100, and a second skin location ii which is adjacent the first skin location i. Alternatively, the apparatus 100 may include two separate patches, e.g. for respectively attaching to non-adjacent first i and second ii skin locations.

As shown in FIG. 2, the apparatus 100 comprises a first sensor 104 for measuring a first concentration ($C_a^i$) of the first analyte at the first skin location i. Similarly to the embodiment shown in FIG. 1, in operation of the apparatus 100 depicted in FIG. 2 sweat is collected from the first skin location i by a first collection hole 106 in the first layer of the patch 102 and transported to the sensor 104 via a channel 108. The channel 108 extends past the first sensor 104 and terminates at an air vent 110 delimited by the second layer of the patch 102.

The first sensor 104 may employ any suitable analyte concentration measurement principle providing the first sensor 104 is able to measure the concentration of the first analyte (a). For example, colorimetry, electrical impedance, or labelled antibodies, etc. may be used in the concentration measurement of the first analyte (a).

In the embodiment shown in FIG. 2, the second sensor for measuring the at least one parameter of sweat excreted by the second sweat gland type at the second skin location ii comprises a flow rate sensor 121. This flow rate sensor 121 may, for instance, comprise a thin channel 131 extending around the patch 102. The thin channel 131 is interposed between the first and second layers of the patch 102, and terminates at an air vent 134 which corresponds to an aperture delimited by the second layer. The thin channel 131 is progressively filled with sweat via a second collection hole 132 at the second skin location ii, and thus provides an indication of the flow rate from the second skin location ii by measurement of the length of the thin channel 131 which becomes filled with sweat as a function of time.

Any suitable detection principle may be used to measure the degree of filling of the thin channel 131. For example, the position of the meniscus in the thin channel 131 as a function of time may be determined from a suitable image. In this respect, the flow rate sensor 121 may include a camera (not shown), and the apparatus 100 may include a controller (not shown in FIGS. 1 and 2) loaded with suitable image analysing software. Alternative flow rate sensing principles may also be contemplated, such as calorimetric flow sensing, temperature gradient driven flow sensing, etc. Such flow rate sensing principles are well-known per se and will not be further described herein for the sake of brevity only.

The inclusion of the flow rate sensor 121 in the apparatus 100 shown in FIG. 2 means that the at least one parameter may include a flow rate of sweat from the second sweat gland type at the second skin location ii. The dilution factor $D_a^i$ may be determined from this measured flow rate.

In other words, the measured flow rate of sweat from the second sweat gland type at the second skin location ii may be used to derive, via the dilution factor $D_a^i$ the real concentration of the first analyte (e.g. solely secreted by the apocrine gland) in the sweat excreted by the first sweat gland (e.g. apocrine sweat) at the first skin location i.

In an embodiment, determining the dilution factor ($D_a^i$) from the flow rate of sweat from the second sweat gland type at the second skin location ii comprises using a predetermined correlation between the flow rate and the dilution factor ($D_a^i$).

In order to attain such a predetermined correlation, a set of volunteers may, for instance, be used. Since these persons will have variable flow rates from glands of the second sweat gland type (e.g. eccrine glands), a correlation may be made of the dilution factor ($D_a^i$) as function of the flow rate of sweat from the second sweat gland type (e.g. eccrine glands) at the second skin location ii.

The apparatus 100 shown in FIG. 1 may, for example, be used to determine the dilution factors ($D_a^i$) of each of the volunteers by measuring the second ($C_e^i$) and third ($C_e^{ii}$) concentrations of the second analyte (e) at the first i and second ii skin locations respectively, as previously described. A suitable flow rate sensor, such as the flow rate sensor 121 described above in relation to the apparatus 100 shown in FIG. 2 may be used to determine the flow rate of sweat from the second sweat gland type at the second skin location ii for each of the volunteers.

A correlation may thus be made between the dilution factor ($D_a^i$) and the flow rate of sweat from the second sweat gland type at the second skin location ii using the data from the volunteers. The resulting (predetermined) correlation may be, for example, in the form of a look-up table or graph, which may then be used determine the dilution factor ($D_a^i$) for a flow rate measured using the flow rate sensor 121 of the apparatus 100 shown in FIG. 2. In turn, the determined dilution factor ($D_a^i$) may then be used to determine the corrected concentration ($C_a$) from the first concentration ($C_a^i$). The predetermined correlation may thus effectively permit extrapolation to zero flow rate from the second sweat gland type (e.g. eccrine glands) at the first skin location i such that the corrected concentration ($C_a$) may be determined.

Whilst use of such volunteer data may lead to lower accuracy for an individual, in certain clinical applications the accuracy may be sufficient. Moreover, in the embodiment shown in FIG. 2, only two sensors are required which may make the apparatus 100 simpler and cheaper to produce. On the other hand, additional concentration sensors, such as the third sensor 112 and the detector 120, as described in relation to the embodiment shown in FIG. 1, and/or further flow rate analysers may optionally be included in the apparatus 100 shown in FIG. 2.

At this point it is noted that the connections to and from the various sensors and detectors in the apparatuses 100 depicted in FIGS. 1 and 2 are not shown for the sake of clarity. These connections may, for instance, include wires for providing power to the sensors and/or for communicating the sensor/detector signals to a controller (not shown in FIGS. 1 and 2) which records/displays the signals via a suitably configured user interface (not shown in FIGS. 1 and 2). Alternatively or additionally, the patch (or patches) 102 may include an on-board chip with an antenna which can receive power wirelessly, and/or transmit the sensor/detector signals wirelessly to the controller recording the signal and/or providing power to the sensors/detectors.

Additional sensors may also be included in the apparatuses 100 shown in FIGS. 1 and 2, which additional sensors may be employed to measure other components originating from the first sweat gland type, i.e. in addition to the first analyte (a). The same techniques as explained above may be used to correct for the dilution due to sweat from glands of the second sweat gland type at the first skin location i.

Figure 3:
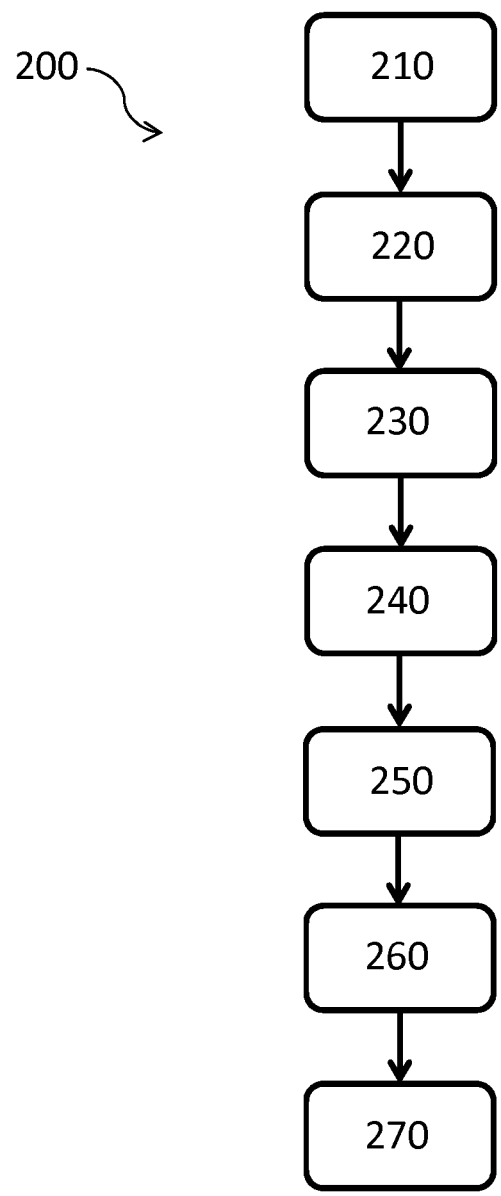
FIG. 3 shows a flowchart of a method according to an embodiment.

FIG. 3 shows a flowchart of a method 200 according to an embodiment. In step 210, a first concentration ($C_a^i$) of the first analyte at a first skin location (i) is measured. This may be achieved using the first sensor 104 of the apparatus 100, as previously described.

In step 220, at least one parameter is measured. The at least one parameter relates to sweat excreted by the second sweat gland type at a second skin location (ii) having the second sweat gland type but not the first sweat gland type. The at least one parameter is then used in step 260 to determine a dilution factor ($D_a^i$) which quantifies dilution of the first analyte by sweat excreted by the second sweat gland type at the first skin location d). In step 270, the first concentration ($C_a^i$) is corrected using the dilution factor ($D_a^i$) so as to provide a corrected concentration ($C_a$) of the first analyte (a).

Measuring 220 the at least one parameter may include measuring a flow rate of sweat from the second sweat gland type at the second skin location. This may be achieved, for instance, using the flow rate sensor 121 of the apparatus 100 shown in FIG. 2. In such a scenario, the using 260 the at least one parameter to determine the dilution factor ($D_a^i$) may comprise using a predetermined correlation between the flow rate and the dilution factor ($D_a^i$), as previously described.

Alternatively or additionally, the method 200 may further comprise measuring 230 a second concentration ($C_e^i$) of a second analyte (e) in sweat excreted by the second sweat gland type at the first skin location (i). This may, for instance, be achieved using the third sensor 112 of the apparatus 100 shown in FIG. 1. In such an embodiment, measuring 220 the at least one parameter includes measuring a third concentration ($C_e^{ii}$) of the second analyte at the second skin location (ii), which may be achieved using the detector 120 of the apparatus 100 shown in FIG. 1.

Using 260 the at least one parameter to determine the dilution factor ($D_a^i$) may comprise calculating the dilution factor ($D_a^i$) using the second concentration ($C_e^i$) and the third concentration ($C_e^{ii}$), e.g. using Equation I, as previously described. Determining 270 the corrected concentration ($C_a$) from the first concentration ($C_a^i$) using the dilution factor ($D_a^i$) may use Equation II.

The method 200 may further include steps which enable anatomical variations in sweat gland density and sweat gland activation levels to be accounted for. Whilst the apparatuses 100 shown in FIGS. 1 and 2 include a single patch 102, this is not intended to be limiting. Alternatively, a first patch may be attached to the first skin location (i) and a second patch may be attached to the second skin location (ii). In such an embodiment, the first sensor 104 is included in the first patch and the second sensor 120, 121 is included in the second patch.

It may be a reasonable assumption that the average secretion rate per gland of the second sweat gland type (e.g. eccrine gland) is equal for nearby skin locations, e.g. spanned by the same patch 102. However, when the two skin locations (i) and (ii) are relatively far apart from each other, the average secretion rates of the second sweat gland type at the respective skin locations may usefully be taken into account.

It has been shown in previous studies, such as by Taylor and Machado-Moreira in "Regional variations in transepidermal water loss, eccrine sweat gland density, sweat secretion rates and electrolyte composition in resting and exercising humans" Extreme Physiology & Medicine 2013; 2:4 (referred to herein below simply as "Taylor"), that although sweating is synchronous across the entire body, eccrine glands from different regions of the body may discharge sweat at different rates. This may in turn imply that there may be a difference in biomarker concentration in the secreted sweat at different regions of the body, which is likely due to anatomical and physiological variations. According to Kondo et al. in "Regional difference in the effect of exercise intensity on thermoregulatory sweating and cutaneous vasodilation" Acta Physiologica Scandinavica 1998, 164:71-78, the level of sweat gland activation can vary between different skin regions with the sweat rate determined by both glandular recruitment and increases in flow rate.

The method 200 may therefore include the following additional steps, which account for regional variations in both the sweat gland density and the sweat gland secretion/discharge rate.

In step 240, a ratio ($R_{act}$) between a first local activation level of glands of the second sweat gland type at the first skin location and a second local activation level of glands of the second sweat gland type at the second skin location may be calculated. In step 250, a value is generated using the at least one parameter and the ratio ($R_{act}$). In this case, the value is used in step 260 to determine the dilution factor ($D_a^i$).

In an embodiment, the ratio ($R_{act}$) is calculated using the following equation:

$$R_{act} = \frac{SR_i^e \cdot GD_{ii}^e}{SR_{ii}^e \cdot GD_i^e};$$ (Equation III)

wherein $SR_i^e$ and $SR_{ii}^e$ are local sweat rates for the glands of the second sweat gland type at the first (i) and second (ii) skin locations respectively, and $GD_i^e$ and $GD_{ii}^e$ are local densities of the glands of the second sweat gland type at the first (i) and second (ii) skin locations respectively.

Equation III may be derived in the following way. The local sweat rate of the second sweat gland type at a given location ($SR_{loc}^e$) may be expressed as:

$$SR_{loc}^e = SR_{ag}^e \cdot N_{ag}^e$$ (Equation F);

wherein $SR_{ag}^e$ is the average sweat rate per activated gland of the second sweat gland type and $N_{ag}^e$ is the average number of activated glands of the second sweat gland type.

$$N_{ag}^e = r_{loc}^e \cdot GD_{loc}^e \cdot A_{patch}$$ (Equation G);

wherein $r_{loc}^e$ is the local ratio of active to inactive glands of the second sweat gland type, $GD_{loc}^e$ is the local sweat gland density of glands of the second sweat gland type (which can, for instance, be derived from Taylor (see Table 3 of Taylor)) and $A_{patch}$ is the patch area (which is a known quantity).

The sweat rate is measured at two different skin locations (i) and (ii), yielding two different sweat rates, $SR_i^e$ and $SR_{ii}^e$, respectively:

$$SR_i^e = SR_{ag;i}^e \cdot N_{ag;i}^e = SR_{ag;i}^e \cdot r_i^e \cdot GD_i^e \cdot A_{patch;i}$$ (Equation H);

$$SR_{ii}^e = SR_{ag;ii}^e \cdot N_{ag;ii}^e = SR_{ag;ii}^e \cdot r_{ii}^e \cdot GD_{ii}^e \cdot A_{patch;ii}$$ (Equation J);

Rearranging Equations H and J gives:

$$SR_{ag;i}^e \cdot r_i^e = \frac{SR_i^e}{GD_i^e \cdot A_{patch;i}};$$ (Equation K)

$$SR_{ag;ii}^e \cdot r_{ii}^e = \frac{SR_{ii}^e}{GD_{ii}^e \cdot A_{patch;ii}}.$$ (Equation L)

Dividing Equation K by Equation L gives:

$$\frac{SR_{a,g;i}^e \cdot r_i^e}{SR_{ag;ii}^e \cdot r_{ii}^e} = \frac{SR_i^e}{SR_{ii}^e} \cdot \frac{GD_{ii}^e \cdot A_{patch;ii}}{GD_i^e \cdot A_{patch;i}};$$ (Equation M)

Assuming for simplicity that $A_{patch;ii} = A_{patch;i}$ (i.e. the patch areas at the two skin locations are the same) and grouping $$\frac{SR_{a,g;i}^e \cdot r_i^e}{SR_{ag;ii}^e \cdot r_{ii}^e}$$

into a single term, $R_{act}$, which captures the ratio of the local activation level of the sweat glands at the two sites, Equation M simplifies to:

$$R_{act} = \frac{SR_i^e}{SR_{ii}^e} \cdot \frac{GD_{ii}^e}{GD_i^e}.$$ (Equation III)

If $r_i^e$ is assumed to equal $r_{ii}^e$ (i.e. the ratio of active to inactive sweat glands at the two sites is the same) then the ratio $R_{act}$ of sweat gland activity $$\left(\frac{SR_{a,g;i}^e}{SR_{ag;ii}^e}\right)$$

at the first and second skin locations may be estimated.

The ratio $R_{act}$ may be used, for instance, to correct the measured (third) concentration of the second analyte ($C_e^{ii}$) at the second skin location (ii), for situations where the assumption that $C_e = C_e^{ii}$ (Equation E) may be less applicable, e.g. where the first and second patches are relatively far apart from each other. In such a scenario, the measured (third) concentration $C_e^{ii}$ may be corrected by multiplying by $R_{act}$. The resulting value may then be used in determining the dilution factor ($D_a^i$) using Equation I.

Alternatively, the ratio $R_{act}$ may be used to correct the measured (second) concentration of the second analyte ($C_e^i$) at the first skin location (i), in which case the (second) concentration $C_e^i$ may be corrected by multiplying by $$\frac{1}{R_{act}}.$$

To implement step 240, the known (average) anatomical second sweat gland density (e.g. eccrine; see Table 3 provided in Taylor) may be used, together with a suitable correlation, e.g. a look-up table, of sweat gland discharge rate with the local sweat rate, the sweat gland density and the sweat gland activity. Such a correlation may be attained from volunteer testing.

In a non-limiting example, when the first and second patches are placed on the forehead and dorsal foot respectively, $R_{act}$ at the peak sweat rate would be, using Equation III:

$$R_{act} = (2.5) * \left(\frac{119}{186}\right) = 1.6$$

The ratio 119/186 was derived from Table 3 provided in Taylor, and the number 2.5 for the ratio $$\frac{SR_i^e}{SR_{ii}^e}$$

has been derived from the graphs shown in FIG. 3 of Taylor. The latter ratio was determined at the peak local sweat rate at 16 minutes for the forehead and for the dorsal foot. Dividing the respective peak heights for the forehead and the dorsal foot gives 2.5.

$R_{act}$=1.6 implies that the sweat gland activity level at the forehead is 1.6 times that at the dorsal foot location. This may suggest that concentration of the second analyte at the forehead is therefore 1.6 times higher than at the dorsal foot.

Figure 4:
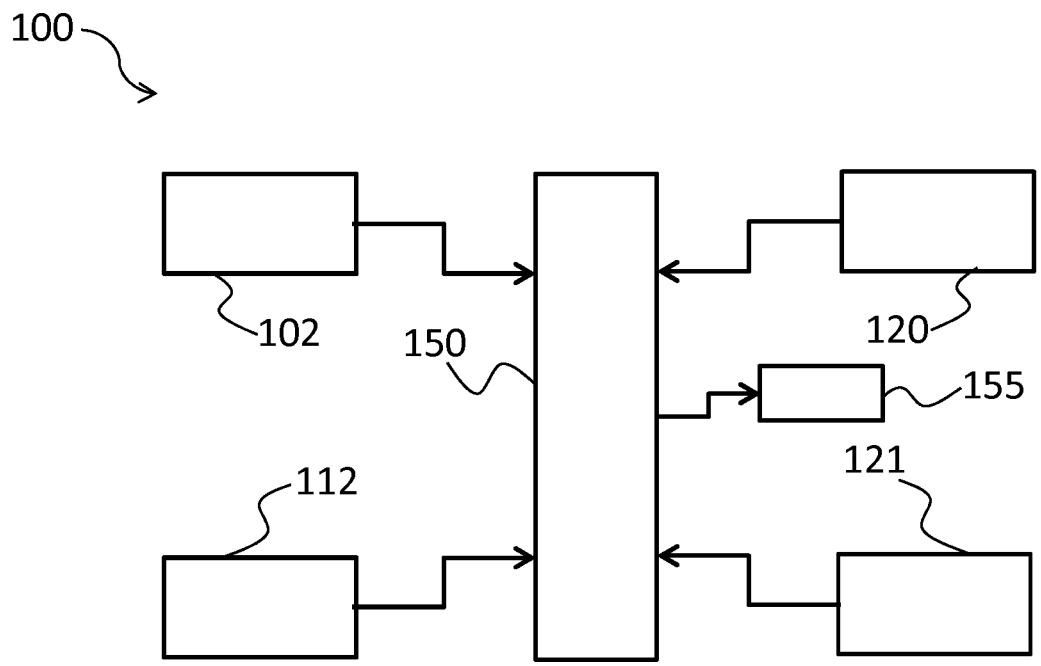
FIG. 4 shows a block diagram of an apparatus according to an embodiment.

FIG. 4 shows a block diagram of an apparatus 100 according to an embodiment. The apparatus 100 includes the first sensor 104 and the second sensor 120, 121, and a controller 150. The controller 150 receives information from the various sensors/detectors included in the apparatus 100, as shown by the arrows pointing from the sensors/detectors to the controller 150. This information may be communicated to the controller 150 via wires or wirelessly, as previously described.

In this embodiment, the controller 150 uses the at least one parameter measured by the second sensor 120, 121 to determine the dilution factor ($D_a^i$). The controller 150 then determines the corrected concentration ($C_a$) from the first concentration ($C_a^i$) using the dilution factor ($D_a^i$). In other words, the controller 150 is configured to implement steps 260 and 270 of the method 200 described above.

When the second sensor comprises the flow rate sensor 121, the controller 150 may determine the dilution factor ($D_a^i$) using the predetermined correlation between the flow rate and the dilution factor ($D_a^i$). The controller 150 may also be configured to detect the meniscus of the sweat in the thin channel 131 from a suitable image, i.e. during the process of determining the flow rate, as previously described.

Alternatively or additionally, when the apparatus 100 includes the third sensor 112 and the detector 120, the controller 150 may determine the dilution factor ($D_a^i$) using the second concentration ($C_e^i$) and the third concentration ($C_e^{ii}$), e.g. using Equation I. The corrected concentration ($C_a$) may then be calculated from the dilution factor ($D_a^i$) and the first concentration ($C_a^i$) using Equation II, as previously described.

In an embodiment, the controller 150 is further configured to implement steps 240 and 250 of the method 200. In this respect, the controller 150 may calculate the ratio ($R_{act}$) between the first local activation level of glands of the second sweat gland type at the first skin location and the second local activation level of glands of the second sweat gland type at the second skin location, e.g. using Equation III. The controller 150 may then generate the value using the at least one parameter and the ratio ($R_{act}$), and determine the dilution factor ($D_a^i$) using the value.

As shown in FIG. 4, the apparatus 100 includes a user interface 155. As shown by the arrow pointing from the controller 150 to the user interface 155, information received and/or computed by the controller 150 may be sent to the user interface 155, which may then display the information. In particular, the user interface 155 may be used to display the corrected concentration ($C_a$) of the first analyte (a) determined by the controller 150. The user interface 155 may include any suitable display type. For example, the user interface 155 may include a LED/LCD display, which may have touchscreen capability permitting entry of parameters by the user, e.g. sweat rate and/or sweat gland density values for use in the $R_{act}$ calculation, and so on.

Figure 5:
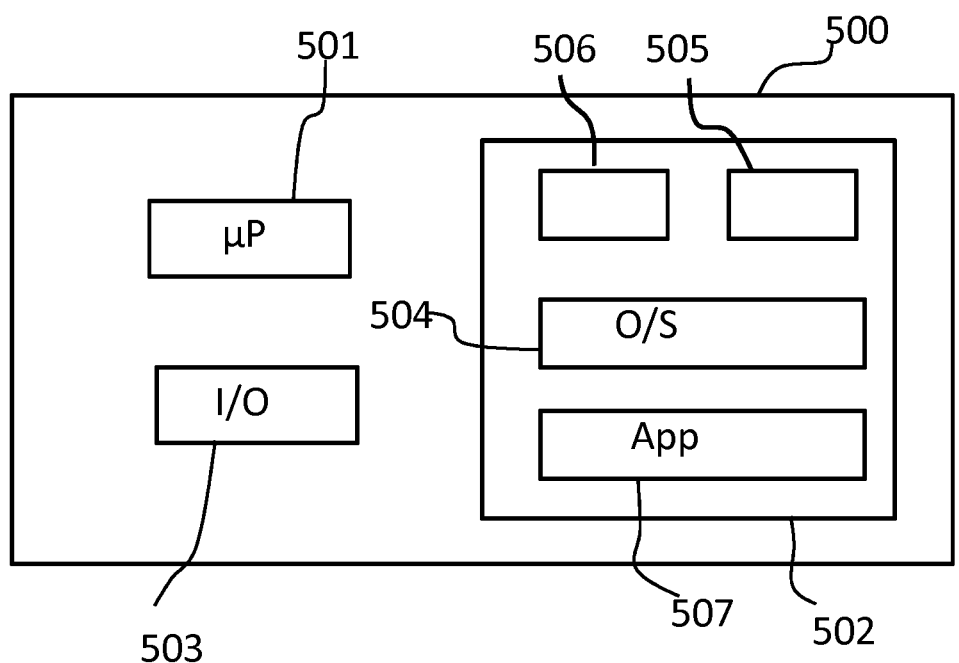
FIG. 5 shows a general computer architecture suitable for implementing the controller used in the apparatus.

FIG. 5 illustrates an example of a computer 500 for implementing the controller 150 described above.

The computer 500 includes, but is not limited to, PCs, workstations, laptops, PDAs, palm devices, servers, storages, and the like. Generally, in terms of hardware architecture, the computer 500 may include one or more processors 501, memory 502, and one or more I/O devices 503 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 501 is a hardware device for executing software that can be stored in the memory 502. The processor 501 can be virtually any custom made or commercially available processor, a central processing unit (CPU), a digital signal processor (DSP), or an auxiliary processor among several processors associated with the computer 500, and the processor 501 may be a semiconductor based microprocessor (in the form of a microchip) or a microprocessor.

The memory 502 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 502 may incorporate electronic, magnetic, optical, and/or other types of storage media. Note that the memory 502 can have a distributed architecture, where various components are situated remote from one another, but can be accessed by the processor 501.

The software in the memory 502 may include one or more separate programs, each of which comprises an ordered listing of executable instructions for implementing logical functions. The software in the memory 502 includes a suitable operating system (O/S) 504, compiler 505, source code 506, and one or more applications 507 in accordance with exemplary embodiments.

The application 507 comprises numerous functional components such as computational units, logic, functional units, processes, operations, virtual entities, and/or modules.

The operating system 504 controls the execution of computer programs, and provides scheduling, input-output control, file and data management, memory management, and communication control and related services.

Application 507 may be a source program, executable program (object code), script, or any other entity comprising a set of instructions to be performed. When a source program, then the program is usually translated via a compiler (such as the compiler 505), assembler, interpreter, or the like, which may or may not be included within the memory 502, so as to operate properly in connection with the operating system 504. Furthermore, the application 507 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 503 may include input devices such as, for example but not limited to, a mouse, keyboard, scanner, microphone, camera, etc. Furthermore, the I/O devices 503 may also include output devices, for example but not limited to a printer, display, etc. Finally, the I/O devices 503 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 503 also include components for communicating over various networks, such as the Internet or intranet.

When the computer 500 is in operation, the processor 501 is configured to execute software stored within the memory 502, to communicate data to and from the memory 502, and to generally control operations of the computer 500 pursuant to the software. The application 507 and the operating system 504 are read, in whole or in part, by the processor 501, perhaps buffered within the processor 501, and then executed.

When the application 507 is implemented in software it should be noted that the application 507 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The present invention may, for instance, be applied in the field of patient monitoring. In particular, the method 200 and apparatus 100 provided herein may be applied as an early warning for sudden deterioration of patients being monitored in a ward, and for investigation of sleep disorders. For the latter, measurements tend only to be done in a spot-check fashion when a patient is visiting a doctor. The present invention may enable continuous or semi-continuous monitoring, which may assist such investigations.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An apparatus comprising:
    a first sensor for measuring a first concentration ($C_a^i$) of a first analyte (a) in sweat excreted by a first sweat gland type at a first skin location (i) having the first sweat gland type and further having a second sweat gland type which does not excrete sweat containing the first analyte, or which excretes sweat having such a low concentration of the first analyte in comparison with the sweat excreted by the first sweat gland type that it can be neglected, or which excretes sweat at a concentration of first analyte which is prima facie significantly different from the concentration of the first analyte in the sweat excreted by the first sweat gland type that the two concentrations can be easily distinguished;
    a second sensor for measuring at least one parameter of sweat excreted by the second sweat gland type at a second skin location (ii) having the second sweat gland type but not the first sweat gland type; and
    a controller configured to:
        use the at least one parameter to determine a factor ($D_a^i$) corresponding to dilution of the first analyte by the sweat excreted by the second sweat gland type at the first skin location; and
        determine the corrected concentration ($C_a$) from the first concentration ($C_a^i$) using the dilution factor ($D_a^i$).

2. The apparatus according to claim 1, wherein the second sensor includes a flow rate sensor and the at least one parameter includes a flow rate of sweat from eccrine glands at the second skin location.

3. The apparatus according to claim 1,
    wherein the second sensor includes a detector for measuring a third concentration ($C_e^{ii}$) of the second analyte in the sweat excreted at the second skin location (ii), the at least one parameter including said third concentration.

4. The apparatus according to claim 1,
    wherein the first sensor and the second sensor are included in a single patch for attaching to the first and second skin locations when said first skin location (i) is adjacent said second location (ii), or
    wherein the first sensor is included in a first patch for attaching to the first skin location (i) and the second sensor is included in a second patch for attaching to the second skin location (ii).

5. The apparatus according to claim 1, wherein, when the second sensor includes a flow rate sensor, the controller is configured to determine the dilution factor ($D_a^i$) using a predetermined correlation between the flow rate and the dilution factor ($D_a^i$).

6. The apparatus according to claim 1, further comprising a third sensor for measuring a second concentration ($C_e^i$) of a second analyte (e) in the sweat excreted at the first skin location (i), the second analyte being in the sweat excreted by the second sweat gland type
    wherein, the controller is configured to calculate said dilution factor using the second concentration ($C_e^i$) and the third concentration ($C_e^{ii}$).

7. The apparatus according to claim 1, wherein the controller is configured to:
    calculate a ratio ($R_{act}$) between a first local activation level of glands of the second sweat gland type at the first skin location and a second local activation level of glands of the second sweat gland type at the second skin location; and
    generate a value using the at least one parameter and the ratio ($R_{act}$), the controller being configured to determine the dilution factor ($D_a^i$) using said value.

8. The apparatus according to claim 6,
    wherein the dilution factor ($D_a^i$) is calculated using the following equation:

$$D_a^i = 1 - \frac{C_e^i}{C_e^{ii}}; \quad \text{(Equation I)}$$

and
wherein the corrected concentration ($C_a$) is calculated from the dilution factor ($D_a^i$) and the first concentration ($C_a^i$) using the following equation:

$$C_a = \frac{C_a^i}{D_a^i}. \qquad \text{(Equation II)}$$

9. The apparatus according to claim 1, wherein the controller is configured to:

calculate a ratio ($R_{act}$) using the following equation:

$$R_{act} = \frac{SR_i^e \cdot GD_{ii}^e}{SR_{ii}^e \cdot GD_i^e}; \qquad \text{(Equation III)}$$

wherein $SR_i^e$ and $SR_{ii}^e$ are local sweat rates for the glands of the second sweat gland type at the first and second skin locations respectively, and $GD_i^e$ and $GD_{ii}^e$ are local densities of the glands of the second sweat gland type at the first and second skin locations respectively; and generate a value using the at least one parameter and the ratio ($R_{act}$), the controller being configured to determine the dilution factor ($D_a^i$) using said value.

\* \* \* \* \*